US011963886B2

(12) United States Patent
Wogoman et al.

(10) Patent No.: US 11,963,886 B2
(45) Date of Patent: Apr. 23, 2024

(54) IMPLANT INSERTION TOOL FOR IMPLANTING AN ACETABULAR COMPONENT AND ASSOCIATED SURGICAL METHOD

(71) Applicant: DEPUY SYNTHES PRODUCTS, INC., Raynham, MA (US)

(72) Inventors: Thomas E. Wogoman, Warsaw, IN (US); Timothy J. Michael, Rolling Prairie, IN (US); Allen W. Robinson, Goshen, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 17/978,364

(22) Filed: Nov. 1, 2022

(65) Prior Publication Data

US 2023/0049470 A1   Feb. 16, 2023

Related U.S. Application Data

(62) Division of application No. 16/430,833, filed on Jun. 4, 2019, now Pat. No. 11,484,416.

(51) Int. Cl.
*A61F 2/46* (2006.01)
(52) U.S. Cl.
CPC .......... *A61F 2/4609* (2013.01); *A61F 2/4603* (2013.01); *A61F 2002/4627* (2013.01)
(58) Field of Classification Search
CPC .................. A61F 2/4603; A61F 2/4609; A61F 2002/4625; A61F 2002/4627
See application file for complete search history.

(56) References Cited

U.S. PATENT DOCUMENTS

| 4,716,894 | A | * | 1/1988 | Lazzeri | A61F 2/4609 606/91 |
| 5,282,805 | A | | 2/1994 | Richelsoph et al. | |
| 5,284,483 | A | | 2/1994 | Johnson et al. | |
| 5,320,625 | A | | 6/1994 | Bertin | |
| 5,584,837 | A | | 12/1996 | Petersen | |
| 6,626,913 | B1 | | 9/2003 | McKinnon et al. | |
| 2007/0123985 | A1 | * | 5/2007 | Errico | A61F 2/4611 623/17.11 |
| 2007/0270973 | A1 | * | 11/2007 | Johnson | A61F 2/4609 623/17.16 |
| 2013/0226186 | A1 | * | 8/2013 | Burgi | A61F 2/4609 606/91 |
| 2014/0276883 | A1 | | 9/2014 | Matyas et al. | |

(Continued)

FOREIGN PATENT DOCUMENTS

DE    69730778 T2    9/2005
EP     2345392 A1    7/2011

OTHER PUBLICATIONS

PCT International Search Report for International Application No. PCT/IB2020/054621, dated Aug. 18, 2020; 9 pages.

*Primary Examiner* — Matthew J Lawson
(74) *Attorney, Agent, or Firm* — Barnes & Thornburg LLP

(57) ABSTRACT

An implant insertion tool for use during a surgical procedure to implant an acetabular cup component into a surgically-prepared acetabulum of a patient's hip includes a metallic elongated shaft, a removable polymeric grip, and a locking nut to secure the grip to the elongated shaft. Such a modular design allows the implant insertion tool to be dissembled prior to sterilization.

9 Claims, 5 Drawing Sheets

(56) References Cited

U.S. PATENT DOCUMENTS

| | | |
|---|---|---|
| 2015/0305891 A1 | 10/2015 | Bergin et al. |
| 2017/0202681 A1* | 7/2017 | Giardiello et al. |
| 2018/0235774 A1* | 8/2018 | Pritchett ............... A61F 2/4609 |
| 2019/0060085 A1* | 2/2019 | Geist ..................... A61F 2/2846 |
| 2020/0383802 A1 | 12/2020 | Wogoman et al. |

* cited by examiner

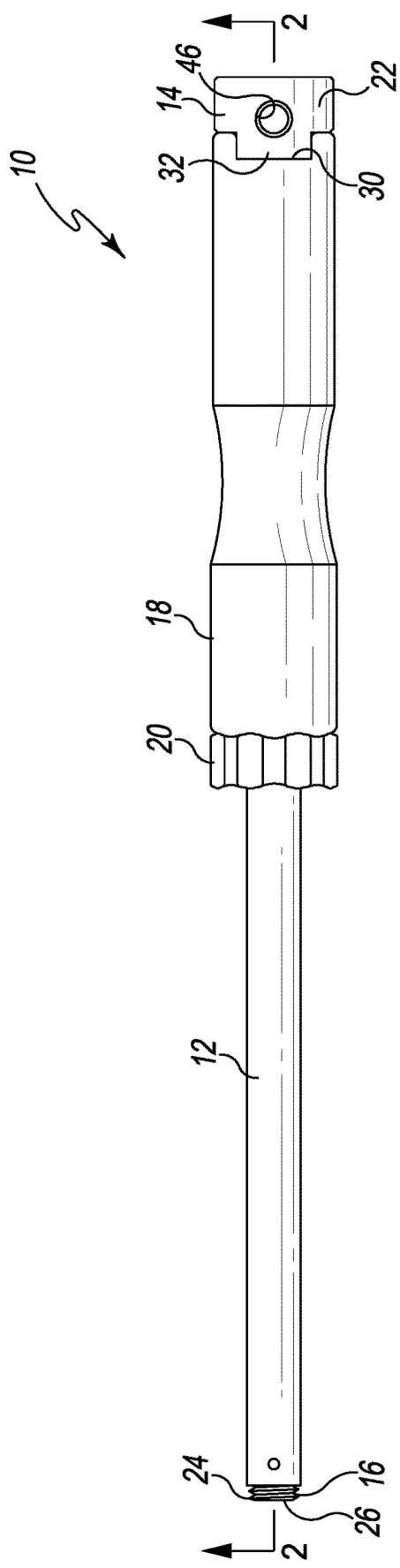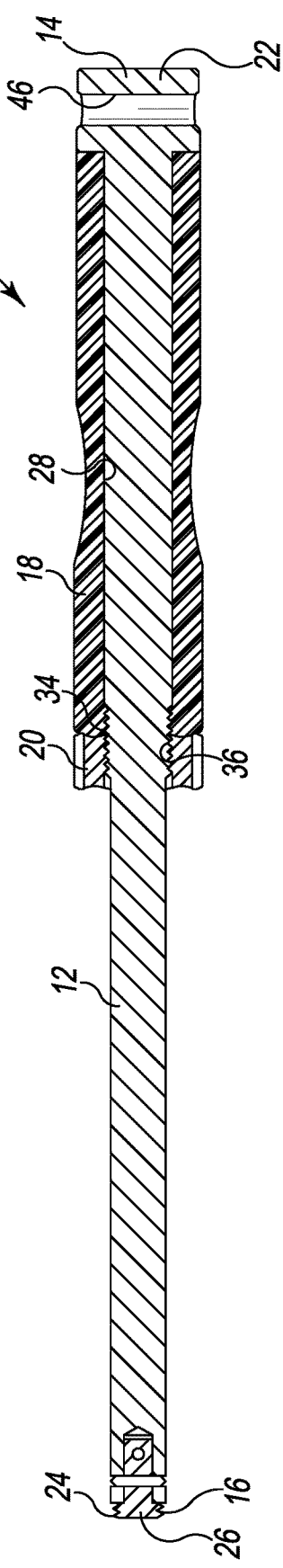

IMPLANT INSERTION TOOL FOR IMPLANTING AN ACETABULAR COMPONENT AND ASSOCIATED SURGICAL METHOD

This application is a divisional of U.S. patent application Ser. No. 16/430,833 filed on Jun. 4, 2019, now U.S. Pat. No. 11,484,416, the entirety of each of which is hereby incorporated by reference.

TECHNICAL FIELD

The present disclosure relates generally to orthopaedic surgical instruments and, more particularly, to surgical instruments used to trial and install an acetabular cup component.

BACKGROUND

Joint arthroplasty is a well-known surgical procedure by which a diseased and/or damaged natural joint is replaced by a prosthetic joint. For example, in a hip arthroplasty surgical procedure, a patient's natural hip ball and socket joint is partially or totally replaced by a prosthetic hip joint. A typical prosthetic hip joint includes an acetabular cup component and a femoral head component. An acetabular cup component generally includes an outer shell configured to engage the acetabulum of the patient and an inner bearing or liner coupled to the shell and configured to engage the femoral head. The femoral head component and inner liner of the acetabular component form a ball and socket joint that approximates the natural hip joint.

To facilitate the replacement of the natural joint with a prosthetic hip joint, orthopaedic surgeons may use a variety of orthopaedic surgical instruments such as, for example, reamers, drill guides, drills, positioners, insertion tools and/or other surgical instruments.

SUMMARY

According to one aspect, an implant insertion tool for use during a surgical procedure to implant an acetabular cup component into a surgically-prepared acetabulum of a patient's hip includes a metallic elongated shaft having an impact head on its proximal end and a set of implant-engaging threads on its distal end. The implant-engaging threads are configured to engage a threaded hole formed in the acetabular cup component. The elongated shaft also includes a set of locking threads formed therein at a location between its proximal end and its distal end. The implant insertion tool also includes a polymeric grip having a bore formed therethrough. The elongated shaft is received into the bore of the grip such that the grip is removably secured to the shaft. The implant insertion tool also includes a locking nut threadingly engaged to the locking threads of the shaft so as to non-rotatably secure the grip to the elongated shaft.

In an embodiment, tightening of the locking nut urges a proximal end of the grip in a direction toward the impact head of the elongated shaft, whereas loosening of the locking nut allows the proximal end of the grip to slide in a direction away from the impact head of the elongated shaft.

In another embodiment, the proximal end of the elongated shaft has a number of flanges formed therein with a proximal end of the grip having a number of slots formed therein. Each of the number of flanges is received into a corresponding one of the number of slots so as to prevent the grip from rotating relative to the elongated shaft.

The elongated shaft may include a body that has the impact head formed therein, with the implant-engaging threads being formed in a tip that is removably secured to the body.

In another embodiment, the implant insertion tool also includes a wrench. An outer annular surface of the locking nut has a number of facets formed therein, whereas the wrench has an engaging surface configured to engage the facets of the locking nut.

The implant insertion tool may also include a pin. In such an embodiment, the proximal end of the elongated shaft has a bore extending therethrough in a direction orthogonal to the longitudinal axis of the shaft, and the pin is positioned in the bore of the shaft so as to create a T-shaped handle for use by a user to counter torque created during use of the wrench.

The distal end of the grip may have a faceted surface formed therein with a proximal end of the locking nut having a faceted surface formed therein. The faceted surface of the locking nut is engaged with the faceted surface of the grip so as to prevent loosening of the locking nut.

In another aspect, an implant insertion tool for use during a surgical procedure to implant an acetabular cup component into a surgically-prepared acetabulum of a patient's hip includes a metallic elongated shaft having an impact head on its proximal end and a set of implant-engaging threads on its distal end. The implant-engaging threads are configured to engage a threaded hole formed in the acetabular cup component. The implant insertion tool also includes a polymeric grip having a bore formed therethrough. The shaft is received into the bore of the grip such that the grip is removably secured to the shaft. A removable fastener is secured to the elongated shaft so as to non-rotatably secure the grip to the elongated shaft.

In such an embodiment, tightening of the fastener urges a proximal end of the grip in a direction toward the impact head of the elongated shaft, whereas loosening of the fastener allows the proximal end of the grip to slide in a direction away from the impact head of the elongated shaft.

The proximal end of the elongated shaft may have a number of flanges formed therein, whereas a proximal end of the grip may have a number of slots formed therein. In such an embodiment, each of the number of flanges is received into a corresponding one of the number of slots so as to prevent the grip from rotating relative to the elongated shaft.

In an embodiment, the elongated shaft includes a body having the impact head formed therein, whereas the implant-engaging threads are formed in a tip that is removably secured to the body.

The implant insertion tool may also include an assembly tool with such an assembly tool having an engaging surface configured to engage the fastener.

The implant insertion tool of may also include a pin. In such an embodiment, the proximal end of the elongated shaft has a bore extending therethrough in a direction orthogonal to the longitudinal axis of the shaft with the pin being positioned in the bore of the shaft so as to create a T-shaped handle for use by a user during use of the assembly tool.

According to another aspect, a method of performing an orthopaedic surgical procedure to implant an acetabular cup component into a surgically-prepared acetabulum of a patient's hip includes assembling an implant insertion tool by sliding a hollow polymeric grip onto a metallic elongated shaft, and thereafter installing a fastener on the elongated shaft so as to non-rotatably secure the grip to the elongated shaft. The acetabular cup component is then secured to the elongated shaft of the assembled implant insertion tool. Thereafter, the acetabular cup component is installed in the patient's hip. The implant insertion tool is then disassembled by removing the fastener from the elongated shaft, and sliding the polymeric grip off of the elongated shaft. Thereafter, the disassembled implant insertion tool is sterilized.

In an embodiment, the elongated shaft has a set of locking threads formed therein at location between its proximal end and its distal end and the fastener is embodied as a threaded locking nut. In such an embodiment, the implant insertion tool is assembled by threading the locking nut to the locking threads of the elongated shaft so as to non-rotatably secure the grip to the elongated shaft.

In an embodiment, an annular surface of the locking nut has a number of facets formed therein, with such a faceted surface being engaged and rotated by a wrench during assembly and disassembly of the implant insertion tool.

In another embodiment, the proximal end of the elongated shaft has a bore extending therethrough in a direction orthogonal to the longitudinal axis of the shaft. During both assembly and disassembly of the implant insertion tool, a pin may be positioned in the bore of the shaft so as to create a T-shaped handle that may be grasped to counter torque created during rotation of the wrench.

In an embodiment, tightening the locking nut urges a proximal end of the grip in a direction toward the proximal end of the elongated shaft, whereas loosening the locking nut allows the proximal end of the grip to slide in a direction away from the proximal end of the elongated shaft.

In an exemplary embodiment, the distal end of the grip has a faceted surface formed therein with a proximal end of the locking nut having a faceted surface formed therein. During assembly of the implant insertion tool, the faceted surface of the locking nut is engaged with the faceted surface of the grip so as to prevent loosening of the locking nut.

In another embodiment, the elongated shaft has an impact head on a proximal end thereof. The impact head of the assembled implant insertion tool is impacted during installation of the acetabular cup component in the patient's hip comprises.

The elongated shaft may have a set of implant-engaging threads on a distal end thereof. The acetabular cup component may be secured to the elongated shaft of the assembled implant insertion tool by threading the implant-engaging threads into a threaded hole formed in the acetabular cup component.

In one embodiment, a proximal end of the elongated shaft has a number of flanges formed therein with a proximal end of the grip having a number of slots formed therein. During assembly of the implant insertion tool, each of the number of flanges is positioned into a corresponding one of the number of slots so as to prevent the grip from rotating relative to the elongated shaft.

In another aspect, an orthopaedic instrument for use during a surgical procedure to implant an orthopaedic prosthesis into a patient includes a metallic elongated shaft and a polymeric grip having a bore formed therethrough. The shaft is received into the bore of the grip such that the grip is removably secured to the shaft. A removable fastener is secured to the elongated shaft so as to non-rotatably secure the grip to the elongated shaft.

In such an embodiment, tightening of the fastener urges a proximal end of the grip in a direction toward proximal end of the elongated shaft, whereas loosening of the fastener allows the proximal end of the grip to slide in a direction away from the proximal end of the elongated shaft.

The proximal end of the elongated shaft may have a number of flanges formed therein, whereas a proximal end of the grip may have a number of slots formed therein. In such an embodiment, each of the number of flanges is received into a corresponding one of the number of slots so as to prevent the grip from rotating relative to the elongated shaft.

The orthopaedic surgical instrument may also include an assembly tool with such an assembly tool having an engaging surface configured to engage the fastener.

The orthopaedic surgical instrument may also include a pin. In such an embodiment, the proximal end of the elongated shaft has a bore extending therethrough in a direction orthogonal to the longitudinal axis of the shaft with the pin being positioned in the bore of the shaft so as to create a T-shaped handle for use by a user during use of the assembly tool.

In an embodiment, the elongated shaft has a set of locking threads formed therein at location between its proximal end and its distal end and the fastener is embodied as a threaded locking nut. In such an embodiment, the implant insertion tool is assembled by threading the locking nut to the locking threads of the elongated shaft so as to non-rotatably secure the grip to the elongated shaft.

In an embodiment, an annular surface of the locking nut has a number of facets formed therein, with such a faceted surface being engaged and rotated by a wrench during assembly and disassembly of the orthopaedic surgical instrument.

In an embodiment, tightening the locking nut urges a proximal end of the grip in a direction toward the proximal end of the elongated shaft, whereas loosening the locking nut allows the proximal end of the grip to slide in a direction away from the proximal end of the elongated shaft.

In an exemplary embodiment, the distal end of the grip has a faceted surface formed therein with a proximal end of the locking nut having a faceted surface formed therein. During assembly of the orthopaedic surgical instrument, the faceted surface of the locking nut is engaged with the faceted surface of the grip so as to prevent loosening of the locking nut.

The orthopaedic surgical instrument may be embodied as any surgical instrument utilized in orthopaedic surgical procedures such as hip, knee, shoulder, or ankle surgical procedures.

BRIEF DESCRIPTION OF THE DRAWINGS

The detailed description particularly refers to the following figures, in which:

FIG. 1 is a side elevational view of an implant insertion tool;

FIG. 2 is a cross sectional view of the implant insertion tool of FIG. 1 taken along the line 2-2 of FIG. 1, as viewed in the direction of the arrows;

DETAILED DESCRIPTION OF THE DRAWINGS

Figure 3:
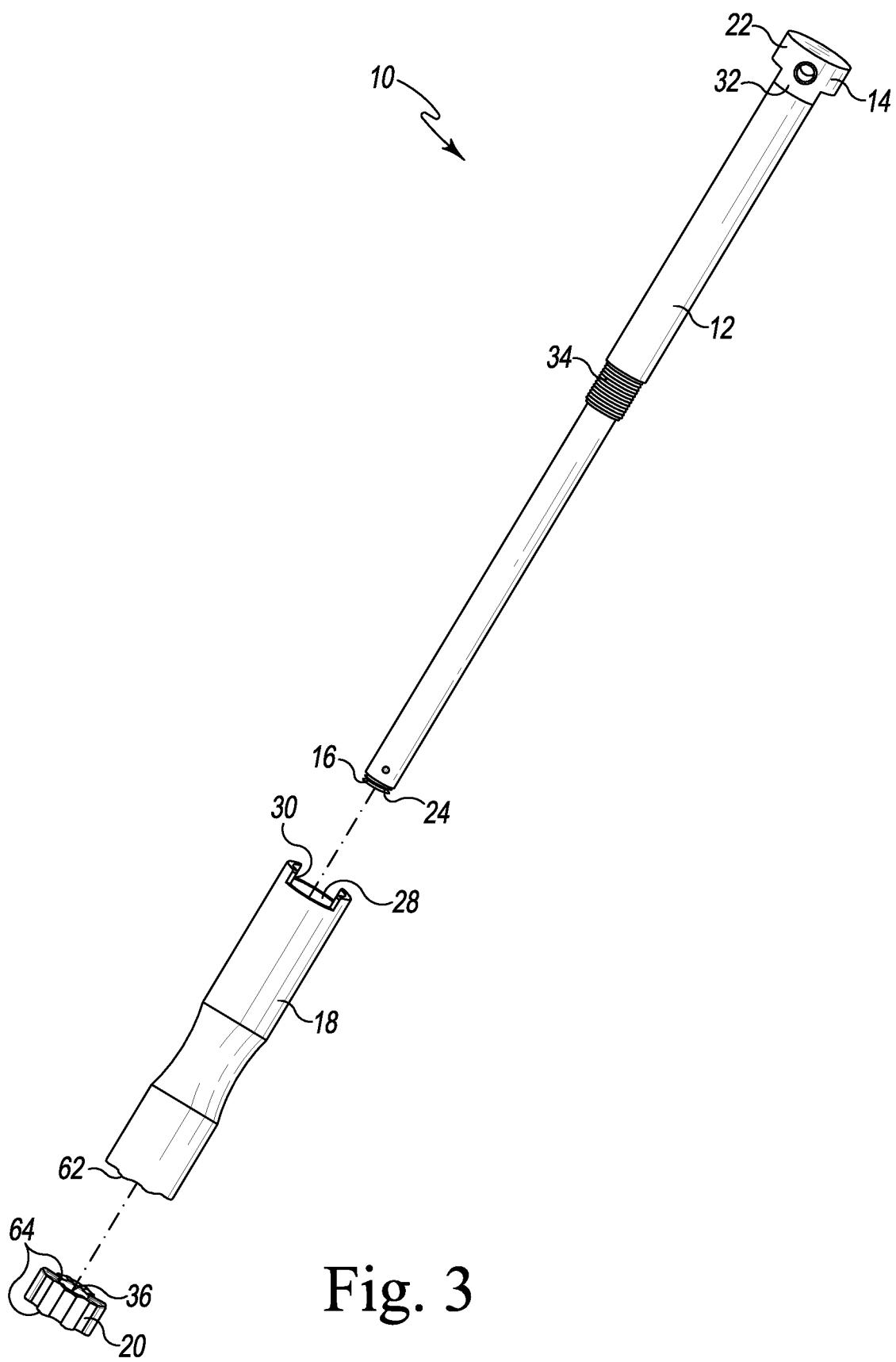
FIG. 3 is an exploded perspective view of the implant insertion tool of FIG. 1.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIGS. 1-3, there is shown an implant insertion tool 10 for inserting an acetabular cup component into the acetabulum of a patient during an orthopaedic surgical procedure. As will be described in more detail below, the components of the implant insertion tool 10 may be disassembled prior to instrument sterilization. In such a way, sterilization of the individual components of the implant insertion tool 10 is enhanced. It should be appreciated that although the concepts of the present disclosure are herein described in regard to an implant insertion tool for use in an orthopaedic hip procedure, the concepts of the present disclosure may be utilized in the design of other types of orthopaedic instruments such as, but not limited to, alignment guides, system handles, removal tools, impactors, or any other type of orthopaedic surgical instrument having a polymeric grip secured to a shaft including instruments used for other types of orthopaedic surgical procedures including knee, shoulder, ankle, or hip procedures.

The implant insertion tool 10 includes a metallic elongated shaft 12 having an impact head 14 on its proximal end and an attachment mechanism 16 on its distal end. A removable polymeric grip 18 is positioned around the outer surface of the insertion tool's shaft 12. The grip 18 allows the surgeon to hold the implant insertion tool 10 during a surgical procedure to implant the acetabular cup component 50. A fastener such as a removable locking nut 20 is threaded onto the insertion tool's shaft 12 to non-rotatably secure the removable grip 18 to the shaft 12.

In the exemplary embodiment described herein, the impact head 14 of the implant insertion tool 10 is embodied a circular metal plate 22 formed in the body of the elongated shaft 12. However, it should be appreciated that the metal plate 22 could be embodied as a separate component welded or otherwise secured to the body of the elongated shaft 12. In use, the surgeon holds the assembled implant insertion tool 10 via the grip 18 and strikes the metal plate 22 with a surgical mallet, sledge, or other impaction tool to drive the acetabular cup component 50 into the patient's surgically-prepared acetabular surface 52 (see FIG. 6). The impact head 14 may also be embodied with one or more flanges extending radially outwardly therefrom (not shown). Such flanges serve to protect the surgeon's hand on the grip 18 during impaction. Moreover, such flanges can be impacted from their underside if the implant insertion tool 10 is used to extract an acetabular cup component 50.

The attachment mechanism 16 of the implant insertion tool 10 is configured to attach to the acetabular cup component 50 during installation of the same in the patient's surgically-prepared acetabular surface 52. Although other mechanisms may be used, in the exemplary embodiment described herein, the attachment mechanism 16 is embodied as a set of threads 24 configured to thread into a threaded hole 56 formed in the acetabular cup component 50 (see FIG. 5) to secure the cup component 50 to the implant insertion tool 10. Like the impact head 14, the threads 24 of the elongated shaft 12 may be formed in the body of the shaft 12 itself. Alternatively, as shown in FIG. 2, the threads 24 of the exemplary embodiment described herein are formed in a separate removable tip 26 that is pinned, screwed, or otherwise secured to the body of the elongated shaft 12. Use of a removable tip 26 allows for replacement threads 24 to be installed on the shaft 12 in cases of thread wear or if a different size thread 24 is needed for a particular application.

As shown in FIG. 2, the grip 18 is embodied as a hollow polymeric sleeve and, as such, has an elongated bore 28 extending through its body. The grip 18 may be installed on the elongated shaft 12 by advancing the distal end of the shaft into the proximal end of the grip's bore 28 (as shown in FIG. 3). The proximal end of the grip 18 has a number of slots 30 formed therein. The slots 30 are sized and shaped to closely correspond to the size and shape of a number of flanges 32 formed in the proximal end of the elongated shaft 12. When the flanges 32 of the shaft 12 are positioned in the slots 30 of the grip 18, the grip 18 and the shaft 12 are prevented from rotating relative to one another.

As shown in FIG. 3, the elongated shaft 12 has a set of locking threads 34 formed in its body at a location between its ends. The locking threads 34 are configured to threadingly engage a set of threads 36 formed in the locking nut 20 (see FIG. 2). In such a way, the locking nut 20 may be used to secure the grip 18 to the elongated shaft 12. In particular, with the grip 18 installed on the elongated shaft 12 such that the flanges 32 of the shaft 12 are positioned in the slots 30 of the grip 18, the locking nut 20 may be slipped onto the distal end of the elongated shaft 12 and advanced proximally into contact with the shaft's locking threads 34. Thereafter, the locking nut 20 may be rotated in a direction that causes the locking nut's threads 36 to engage the locking threads 34 of the shaft 12. Continued tightening of the locking nut 20 urges it proximally in the direction toward the shaft's proximal end and hence the impact head 14. In such a way, the grip 18 is clamped between the locking nut 20 and the impact head 14. As such, the grip 18 is non-rotatably secured to the elongated shaft 12. That is, the grip 18 is prevented from moving linearly or rotating relative to the elongated shaft 12.

Removal of the grip 18 may be accomplished by first removing the locking nut 20. To do so, the locking nut 20 is rotated in the opposite direction thereby loosening the threaded connection between the locking nut 20 and the elongated shaft 12. More specifically, the locking nut 20 may be rotated in the direction that causes the locking nut's threads 36 to disengage the locking threads 34 of the shaft 12. Once the threads 34, 36 disengage one another, the locking nut 20 may be slipped off the distal end of the elongated shaft 12. Removal of the locking nut 20 removes the clamping force from the grip 18 thereby allowing it to be likewise slipped off the distal end of the elongated shaft 12.

As can be seen in FIG. 3, the end face formed in the distal end of the grip 18 (i.e., the surface that faces the locking nut 20) has a faceted surface 62 formed therein. Both end faces of the locking nut 20 have a faceted surface 64 formed therein. As such, irrespective of which direction/side the locking nut 20 is installed on the elongated shaft 12, one of the faceted surfaces 64 is positioned on the proximal end of the locking nut 20 (i.e., the faceted surface 64 that faces the grip 18). As such, irrespective of which direction/side of the locking nut 20 is installed on the elongated shaft 12, one of the faceted surfaces 64 engages the faceted surface 62 of the grip 18 during tightening of the locking nut 20. Such engagement of the complimentary faceted surfaces 62, 64 prevents the locking nut 20 from loosening during repeated strikes of the impact head 14 during installation of the acetabular cup component 50.

Figure 4:
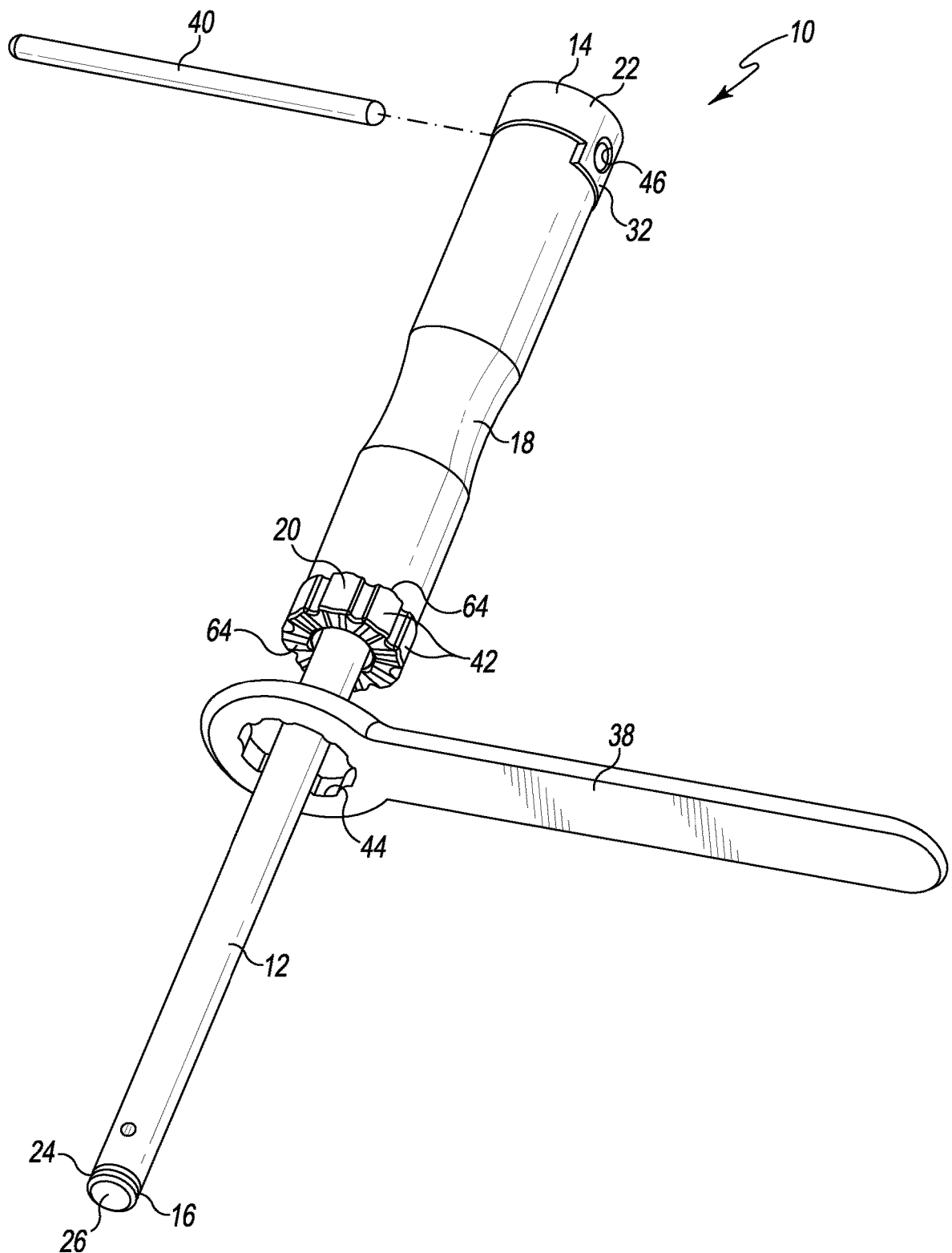
FIG. 4 is perspective view of the implant insertion tool of FIG. 1 showing the wrench and pin used during installation or removal of the implant insertion tool's locking nut.

As can be seen in FIG. 4, a pair of assembly tools such as a wrench 38 and a pin 40 may be utilized to facilitate installation and removal of the locking nut 20. The locking nut 20 has an annular outer surface profile defined by a number of facets 42 formed therein. The wrench 38 has a complimentary engaging surface 44 that is configured to engage the facets 42 of the locking nut 20 so as to firmly grip the locking nut's annular outer surface. In such a way, a user can utilize the wrench to grip the locking nut 20 to apply torque to it during tightening and loosening of the locking nut 20.

The pin 40 is sized and shaped to be received into a bore 46 that is formed in the proximal end of the elongated shaft 12 at a location proximate to the impact head 14. As can be seen in FIGS. 1 and 2, the bore 46 extends through the elongated shaft 12 in a direction that is orthogonal to the shaft's longitudinal axis. Insertion of the pin 40 into the bore 46 creates a T-shaped handle for a user to grip during use of the wrench 38 or manual rotation of the locking nut 20. Such a T-shaped handle allows the user to counter the torque created during tightening or loosening of the locking nut 20.

The metallic components of implant insertion tool 10 (e.g., the elongated shaft 12, the locking nut 20, the wrench 38, and the pin 40) may be constructed from a medical-grade metal such as stainless steel, cobalt chrome, or titanium, although other metals or alloys may be used. Moreover, in some embodiments, rigid polymers such as polyetheretherketone (PEEK) may also be used. The grip 18 may be constructed from a polymer such as polyoxymethylene (POM), silicone rubber, thermoplastic rubber, along with other suitable medical grade polymers.

In use, the implant insertion tool 10 may be utilized by a surgeon to implant the acetabular cup component 50 into the surgically-prepared acetabulum 52 of a patient. The surgeon or a member of the surgical team initially assembles the implant insertion tool 10 by installing the grip 18 on the elongated shaft 12 such that the flanges 32 of the shaft 12 are positioned in the slots 30 of the grip 18. Thereafter, the locking nut 20 is slipped onto the distal end of the elongated shaft 12 and advanced proximally into contact with the shaft's locking threads 34. The pin 40 is then inserted into the bore 46 to create a T-shaped handle which the surgeon grips as the surgeon uses the wrench 38 to tighten the locking nut 20. Tightening of the locking nut 20 clamps the grip 18 between the locking nut 20 and the impact head 14 thereby non-rotatably securing it to the elongated shaft 12.

Figure 5:
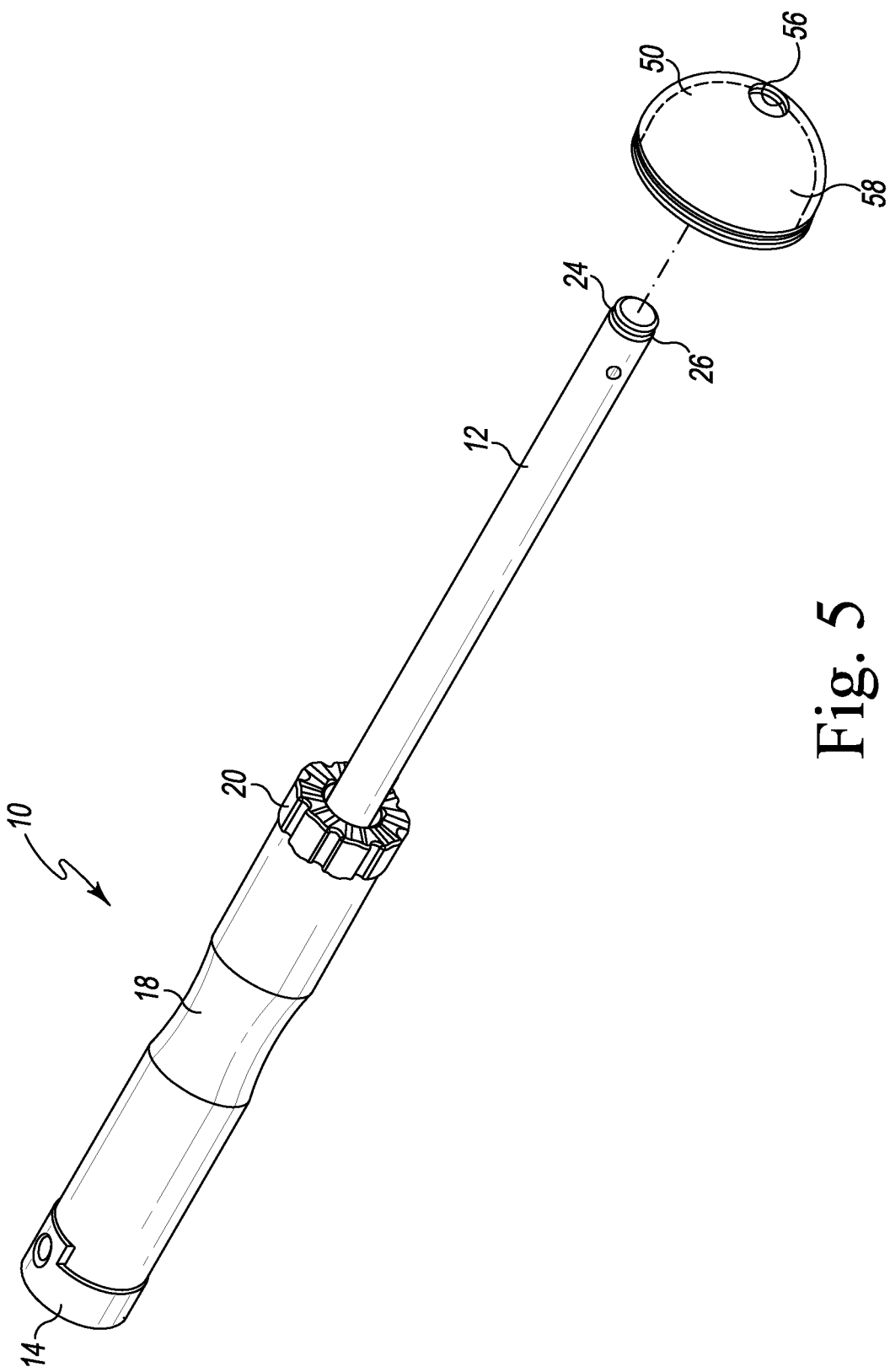
FIG. 5 is a perspective view showing an acetabular cup component being secured to the implant insertion tool of FIG. 1.

Once the implant insertion tool 10 has been assembled in such a manner, the surgeon secures the acetabular cup component 50 to the tool 10. Specifically, as shown in FIG. 5, the threads 24 of the elongated shaft 12 of the tool 10 are threaded into the threaded hole 56 formed in the acetabular cup component 50 and thereafter tightened to secure the cup component 50 to the implant insertion tool 10.

Figure 6:
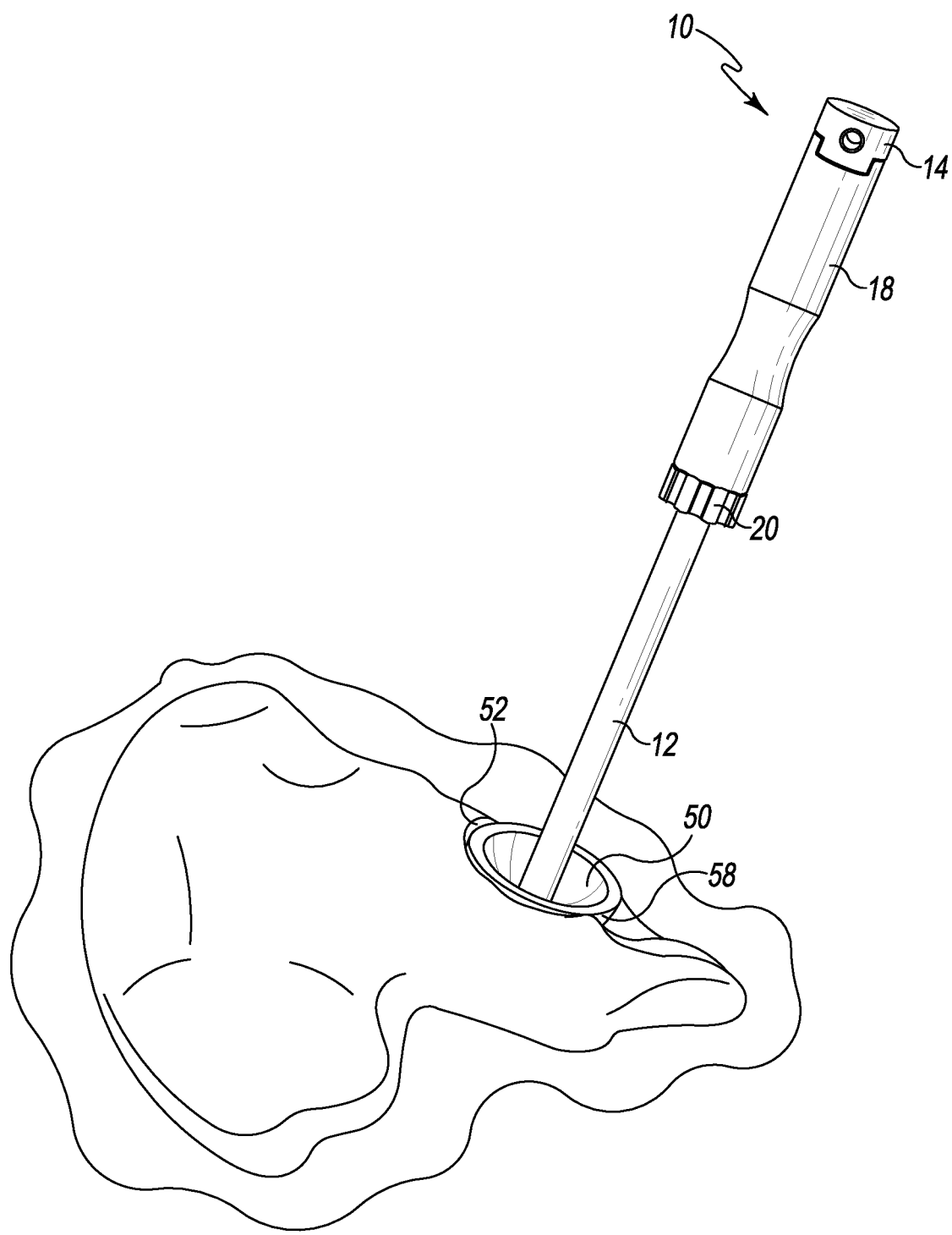
FIG. 6 is a perspective view showing the acetabular cup component being installed in the acetabulum of a patient's hip by use of the implant insertion tool of FIG. 1.

Thereafter, as shown in FIG. 6, the surgeon uses the implant insertion tool 10 to position the acetabular cup component 50 such that its generally hemispherically-shaped bone-engaging surface 58 is inserted into the patient's surgically-prepared acetabular surface 52 in a desired orientation. Once the acetabular cup component 50 is positioned in such a manner, the surgeon strikes the impact head 14 of the implant insertion tool 10 with a surgical mallet, sledge, or other impaction tool to drive the acetabular cup component 50 into the bone tissue until the acetabular cup component 50 is fully seated in the patient's surgically-prepared acetabular surface 52.

The surgeon then releases the acetabular cup component 50 from the implant insertion tool 10. To do so, the surgeon rotates the implant insertion tool 10 in a direction that loosens (i.e., unthreads) the threads 24 of the elongated shaft 12 of the tool 10 from the threaded hole 56 of the acetabular cup component 50.

The implant insertion tool 10 is then disassembled. To do so, the pin 40 is inserted into the bore 46 to create a T-shaped handle which the surgeon grips as the surgeon uses the wrench 38 to loosen the locking nut 20. Loosening the locking nut 20 causes the locking nut's threads 36 to disengage the locking threads 34 of the shaft 12. Once the threads 34, 36 disengage one another, the locking nut 20 may be slipped off the distal end of the elongated shaft 12. Removal of the locking nut 20 removes the clamping force from the grip 18 thereby allowing it to be likewise slipped off the distal end of the elongated shaft 12.

The components of the disassembled implant insertion tool 10—i.e., the elongated shaft 12, the grip 18, and the locking nut 20—may then be sterilized. Specifically, the elongated shaft 12, the grip 18, and the locking nut 20 may be sterilized individually or as a group but in a disassembled state. Once each of the components of the disassembled implant insertion tool 10 has been sterilized, the implant insertion tool 10 may be reassembled for use in a subsequent surgical procedure.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

For example, the fastener for securing the grip 18 to the elongated shaft 12 is herein described as the locking nut 20 with such a fastener having significant advantages in regard to the design of the implant insertion tool 10. However, it should be appreciated that certain of such advantages may be realized by the use of other fasteners such as clips, pins, slip-type connectors, locking collars, or the like.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. A method of performing an orthopaedic surgical procedure to implant an acetabular cup component into a surgically-prepared acetabulum of a patient's hip, comprising:

assembling an implant insertion tool by (i) sliding a smooth bore of a hollow polymeric grip onto a metallic elongated shaft, wherein (a) the bore extends from a distal end of the grip to a proximal end of the grip, (b) the elongated shaft has an impact head on its proximal end and a set of implant-engaging threads on its distal end, and (c) the grip comprises an elongated outer surface that extends parallel to the grip's bore and is configured to be gripped during impaction of the elongated shaft's impact head, and (ii) installing a fastener on the elongated shaft so as to clamp the grip between the fastener and the elongated shaft's impact head thereby non-rotatably securing the grip to the elongated shaft, securing the acetabular cup component to the implant-engaging threads of the elongated shaft of the assembled implant insertion tool, installing the acetabular cup component in the patient's hip, disassembling the implant insertion tool by (i) removing the fastener from the elongated shaft, and (ii) sliding the polymeric grip off of the elongated shaft, and sterilizing the disassembled implant insertion tool.

2. The method of claim 1, wherein:

the elongated shaft has a set of locking threads formed therein at location between a proximal end and a distal end thereof, the fastener comprises a threaded locking nut, and assembling the implant insertion tool comprises threading the locking nut to the locking threads of the elongated shaft so as to non-rotatably secure the grip to the elongated shaft.

3. The method of claim 2, wherein:

the locking nut has a number of facets formed therein, assembling the implant insertion tool comprises (i) engaging a wrench to the facets of the locking nut, and (ii) rotating the wrench in a first direction so as to tighten the locking nut, and disassembling the implant insertion tool comprises (i) engaging the wrench to the facets of the locking nut, and (ii) rotating the wrench in a direction opposite the first direction so as to loosen the locking nut.

4. The method of claim 3, wherein:

the proximal end of the elongated shaft has a bore extending therethrough in a direction orthogonal to the longitudinal axis of the shaft, and both assembling the implant insertion tool and disassembling the implant insertion tool comprises (i) positioning a pin in the bore of the shaft so as to create a T-shaped handle, and (ii) grasping the T-shaped handle to counter torque created during rotation of the wrench.

5. The method of claim 2, wherein:

assembling the implant insertion tool comprises tightening the locking nut so as to urge a proximal end of the grip in a direction toward the proximal end of the elongated shaft, and disassembling the implant insertion tool comprises loosening the locking nut so as to allow the proximal end of the grip to slide in a direction away from the proximal end of the elongated shaft.

6. The implant insertion tool of claim 2, wherein:

a distal end of the grip has a faceted surface formed therein, a proximal end of the locking nut has a faceted surface formed therein, and assembling the implant insertion tool comprises engaging the faceted surface of the locking nut with the faceted surface of the grip so as to prevent loosening of the locking nut.

7. The method of claim 1, wherein:

installing the acetabular cup component in the patient's hip comprises impacting the impact head of the assembled implant insertion tool.

8. The method of claim 1, wherein:

securing the acetabular cup component to the elongated shaft of the assembled implant insertion tool comprises threading the implant-engaging threads into a threaded hole formed in the acetabular cup component.

9. The method of claim 1, wherein:

the proximal end of the elongated shaft has a number of flanges formed therein, the proximal end of the grip has a number of slots formed therein, and assembling the implant insertion tool comprises positioning each of the number of flanges into a corresponding one of the number of slots so as to prevent the grip from rotating relative to the elongated shaft.

* * * * *